United States Patent [19]

Matsushiro

[11] Patent Number: 5,968,772
[45] Date of Patent: Oct. 19, 1999

[54] PEARL PROTEIN (NACREIN) AND PROCESS FOR PRODUCING THE SAME

[76] Inventor: Aizo Matsushiro, 15-12, Aoyamadai 4 chome, Suita-shi, Osaka 565, Japan

[21] Appl. No.: 08/945,848
[22] PCT Filed: May 9, 1996
[86] PCT No.: PCT/JP96/01236
§ 371 Date: Jan. 13, 1998
§ 102(e) Date: Jan. 13, 1998
[87] PCT Pub. No.: WO96/35786
PCT Pub. Date: Nov. 14, 1996

[30] Foreign Application Priority Data

May 9, 1995 [JP] Japan ..................................... 7-110877

[51] Int. Cl.⁶ ........................... C12P 21/06; C07H 17/00; C07K 14/00
[52] U.S. Cl. .......................... 435/69.1; 536/23.1; 530/350
[58] Field of Search ........................... 435/69.1; 536/23.1; 530/350

*Primary Examiner*—Karen Cochrane Carlson
*Attorney, Agent, or Firm*—Marshall, O'Toole, Gerstein, Murray & Borun

[57] ABSTRACT

A nacrein protein is expressed by separating a protein fraction having a molecular weight of sixty thousand, as determined by SDS-PAGE, from pearl proteins extracted from the nacreous layers of pearl oysters, synthesizing a probe coding for the N-terminal amino acid sequence of the protein in this fraction, cloning the cDNA derived from the mRNA of the mantle of the pearl oyster and hybridizable with the synthesized probe, and introducing the cloned cDNA into the host cells of *Escherichia coli*.

11 Claims, 12 Drawing Sheets

① ②

```
nacrein   1   MYLHLTALCV VIPLCYGASM FKHDHYMDNG VRYPNGDGIC KQLNETKCDA GFSYDRSICE
CA2       1   ---------- ---------- ---------- ---------- ---------- SHHWGYGKHN nacrein  61   GPHYWHTISK CF-IACGIGQ RQSPINIVSY DAKFRQRLPK LKFKPHMEKL KTEVTNHQN-
                     *  ****   * **       *       **             *    
CA2      11   GPEHWH---K DFPIA--KGE RQSPVDIDTH TAK---YDPS LKPLSVSYDQ ATSLRILNNG nacrein 119   RAPEFEPEDG ENLYVKLNNL VDGHYKFHNL HMHNGRTRRK GSEHSVNGRF TPMEAHLVFH
                  *      *           *         * *      ****          *  * * 
CA2      63   HAFNVEFDDS QDKAVLKGGP LDGTYRLIQF HFHWGSLDGQ GSEHTVDKKK YAAELHLV-- nacrein 179   HDDQTHFEPT RTKLGGAFPG HNDFVVVGVF LEVGDDGFGD EPDDEECKHI LKGHHPDNNE
                       *   *            *          *        *
CA2     121   ----HWNTK YGDFGKAVQQ POGLAVLGIF LKVGSAKPGL QKVVDVLDSI ---------- nacrein 239   NGNGDNGNNG YNGDNGNNGD NGNNSYNGDN GNNGVNGNNG YNGDNGNNGD NGNNGYNGQN

CA2     166   ---------- ---------- ---------- ---------- ---------- ---------- nacrein 299   GNNGDNGNNG ENGNNGENGN NGENGHKHGC RVKKAKHLSR ILECAYRNDK VREFKKVGEE
                                                  * *                *       
CA2     166   ---------- ---------- ---KTKGKS- ---ADFTNFD PR-------- ---------- nacrein 359   EGLDVHLTPE MALPPLKYRH YYTYEGSLTT PPCTESVLHV VQKCHVQV-S RRVL-HALRN
              *  *       *          *  ***  *    *  *           *       * 
CA2     181   ----GLLPE- ---SLD--- YWTYPGSLTT PPLLECVTWI VLKEPISVSS EQVLKFRKLN nacrein 417   VEGYKDGTTL RKYGTRRPTQ KNKVTVYK-S FK
                *             *       * *      **
CA2     229   FNGEGEPEEL -MVDNWRPAQ PLKNRQIKAS FK
```

Fig. 10

[ABBREVIATION]  A : NACREIN SYNTHESIZED IN E.coli.

C : NACREIN OBTAINED FROM NATURAL PEARL.

B : BAND ON PROTEIN HAVING NON-SPECIFIC REACTIVITY TO ANTI-NACREIN ANTIBODY.

I : EXPRESSION OF NACREIN IN E.coli.
  + : EXPRESSED SAMPLE (LANE1)
  − : NON-EXPRESSED SAMPLE (LANE2)

II : COMPARISON ON NACREIN FROM NATURAL SOURCE (60kD : LANE2) AND THAT SYNTHESIZED IN E .coli (50kD : LANE1)

PEARL PROTEIN (NACREIN) AND PROCESS FOR PRODUCING THE SAME

This application has been filed under 35 U.S.C. 371 from PCT/JP96/01236, filed May 9, 1996, which claims priority to Japanese Patent Application 7-110877, filed May 9, 1995.

TECHNICAL FIELD

The present invention relates to proteins of constituting the pearl (pearl proteins), especially, to nacrein proteins produced through the genetic engineering techniques, and to a process for producing and expressing the proteins.

BACKGROUND ART

Shell of the pearl layer in the pearl oyster is consisting of minor proteinic organic matrix and crystal of aragonite. This organic matrix had been designated as "Conchiolin" (Fremy, M. E., Recherches chimiques sur les os. Ann. Chem. Phys, 43, 96 (1855)) and have been studied by many persons since then in all its aspects.

See, for example, the publications of:

(1) Cariolou, M. A. & Morse, D. E., "Purification and Characterization of calcium-binding conchiolin shell peptides from the mollusc, Haliotis rufescens, as a function of development", J. Comp. Physiol. B, 157, pp. 717–729 (1988);

(2) Samata, T. & Krampitz G, "Ca-binding polypeptides in oyster shells", Malacologia 22, pp. 225–233 (1981);

(3) Samata, T., "Ca-binding glycoproteins in molluscan shells with different types of ultrastructure", The Veliger 33, pp. 190–201 (1990);

(4) Koji WADA, "Pearl", Association of Jewelogy of Japan (1982);

(5) Weiner, S. & Hood, L., "Soluble protein of the organic matrix of mollusk shells: a potential template for shell formation", Science, 190, pp. 987–989 (1975);

(6) Weiner, S. & Lowenstam, H. A., "Discrete molecular weight components of the organic matrices of mollusc shells", J. exp. mar. Biol. Ecol., 30, pp. 45–51 (1977);

(7) Weiner, S., "Aspartic acid rich proteins: major component of the soluble organic matrix of mollusc shells", Calicif. Tissue Int., 29, pp. 163–167 (1979); and (8) Weiner, S., "Mollusk shell formation: isolation of two organic matrix proteins associated with calcite deposition in the bivalve, Mytilus calfornianus", Biochemistry, 22, pp. 4139–4145 (1983).

Up to date, although it was reported that one of the main components in the organic matrix of the pearl layer is asparatic acid rich acidic protein in the molecular weight of 50~70 kD [See, publications (3) and (7) listed above], its accurate molecular weight and the amino acid sequence thereof have not been reported at all.

Accordingly, as a popular technology for forming pearl wherein a part of shell of *Pinctada fucata* is coaggulated, cultivation methods depending on environmental (cultural) conditions have been employed over one century or more to cultivate *Pinctada fucata* for one to two year(s) in a hanging sack in the sea.

DISCLOSURE OF INVENTION

The present invention is established to solve the problems noted above. That is to say, in addition to the genetical study/analysis of the pearl proteins, it is aimed to artificially produce the pearl proteins based on the unique genetic information of such proteins.

At the first step, the inventor extracted the substantial proteins from the natural pearl, purified them and isolated an acidic protein (nacrein) in the molecular weight of approximately 60,000 which is one of the major elements of the proteins and have $Ca^{2+}$ (calcium ion) binding activity. Then, the N-terminal amino acids sequence of this protein was determined, then DNA probes corresponding to the sequence was synthesized.

On the other hand, cDNA library was constructed by extracting mRNA from mantle tissues of *Pinctada fucata* involved with production of the natural pearl layer. cDNA of nacrein was cloned from this library by a hybridization technique utilizing the synthesized DNA probes noted above.

Then, the nacrein was produced according to the known technique by linking cDNA so obtained to a gene expression vector and introducing the vector into host cell like *E. coli*. Watabe and Wilbur had already reported that the crystal of aragonite would be specifically produced on the organic matrix of the pearl layer (Watabe N. and Wilbur K. N., "Influence of the organic matrix on crystal type in Molluscs", Nature 188, 334 (1960)). Further, in view of the facts that the nacrein is one of the essential elements of the organic matrix and is the protein having $Ca^{2+}$-binding activity, in vitro production of the pearl layer will be realized by crystallizing the calcium carbonite to aragonite on the protein.

BRIEF DESCRIPTION OF DRAWINGS

FIG. 10 reveals homology between the amino acids of the nacrein and that of the carbonic anhydrase.

BEST MODE FOR CARRYING OUT THE INVENTION

The present invention will be described in detail along with the Examples, but the inventions should not be limited based on the disclosure of such Examples.

EXAMPLE 1

Extraction and Purification of Nacrein Protein

Figure 1:
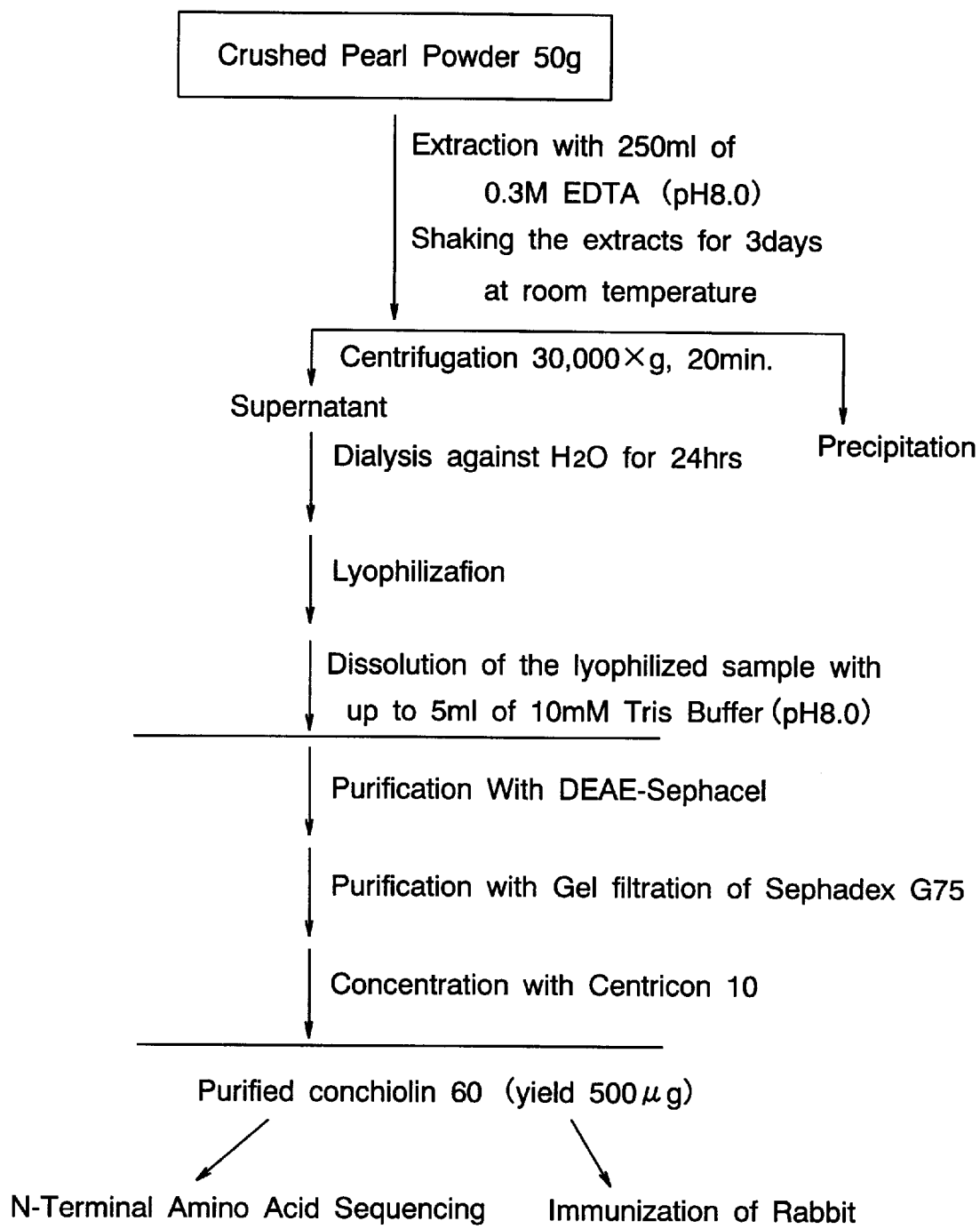
FIG. 1 is a scheme showing an outline for extraction, concentration and purification of the nacrein proteins.

Extraction, concentration and purification of the nacrein protein was performed along with the procedures schematically shown in the FIG. 1.

① Extraction and Concentration of Protein Sample

Clean pearls were selected from crude pearls and nucleus of the pearls were removed. Then, approximately 50 g of powdered strating materials were prepared by isolating pearl layers and crushing them with a pestle. 250 ml of 0.3M ethylenediaminetetraacetic acid (EDTA, pH 8.0) containing 0.01% sodium azide was added to the starting materials, then a mixture was shaked for about three days at room temperature, and soluble organic matrix was extracted therefrom.

This extracted solution was centrifuged at 30,000 g for 20 minutes. Supernatant thereof was poured into a dialysis tube (Spectropore 6, Separation Molecular Weight=2,000) and was dialyzed with $H_2O$ at 4° C. for 24 hours ($H_2O$ of outer dialysis solution was changed twice). Then, each of approximately 50 ml of inner dialysis solution was poured into an egg-plant type flask and was lyophilized. Lyophilized samples were dissolved in approximately 8 ml of 10 mM Tris Buffer (pH 8.0) and the products so obtained were used as samples for an ion-exchange chromatography.

Figure 2:
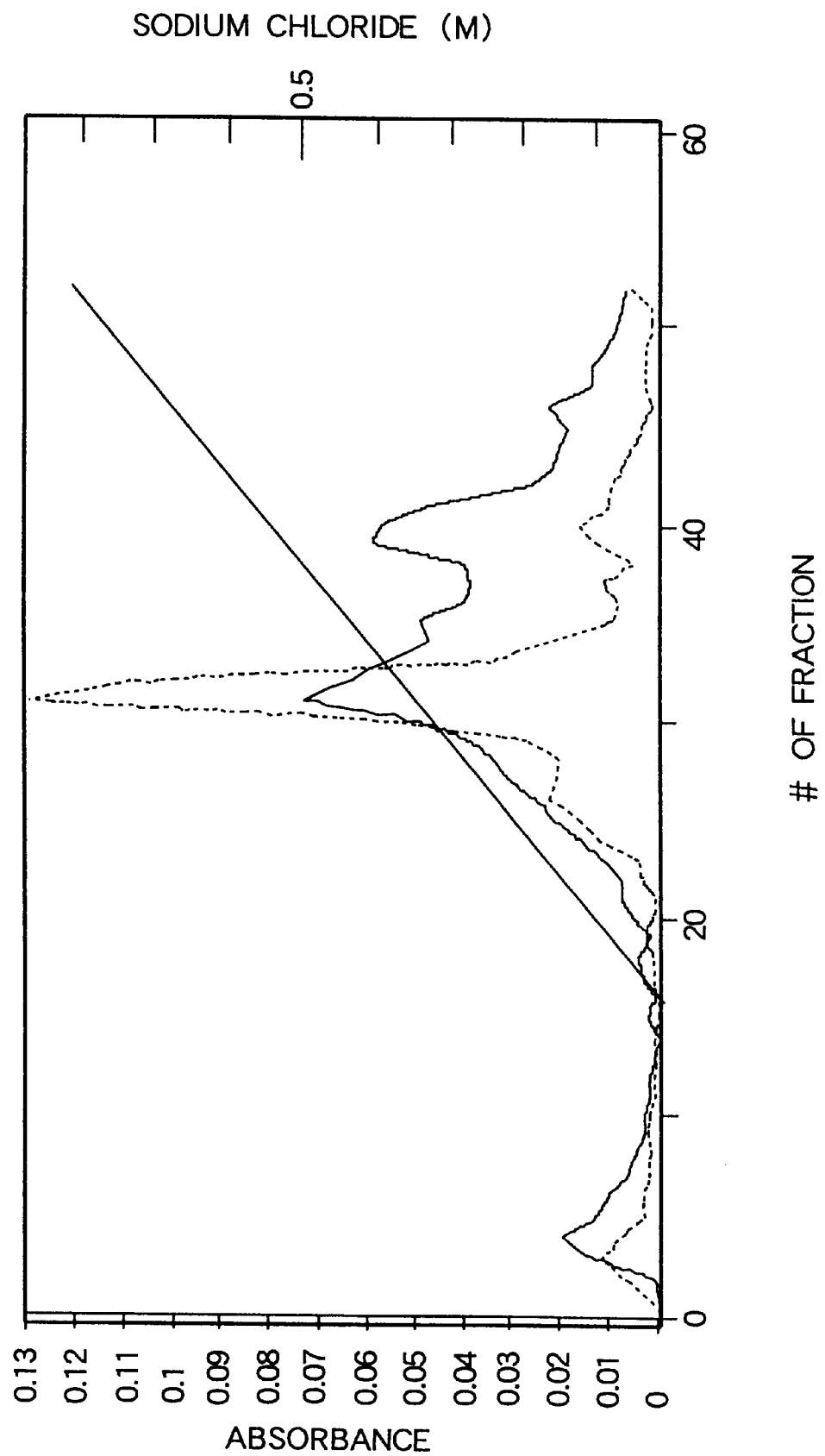
FIG. 2 is a graph showing an elution curve of the nacrein proteins obtained by DEAE-Sephacel Column Chromatography.

② Purification of Nacrein Protein 4 ml of aforementioned sample was poured into DEAE-Sephacel Column (Ø15 mm×120 mm) equilibrated with 10 mM EDTA solution (pH 7.0) and the proteins in the sample was adsorbed thereby. After washing the column with EDTA solution, extraction was performed with a linear gradient (400 ml) of 0~0.8M sodium chloride (10 mM EDTA, pH 7.0) and extracts were collected as 8 ml fractions. FIG. 2 shows an extraction pattern obtained by the chromatography of these fractions. In FIG. 2, the solid line is directed to an absorbance at 280 nm wavelength, while the dot line is directed to a quantitative curve on proteins by TCA method ($\mu$=340 nm).

Figure 3:
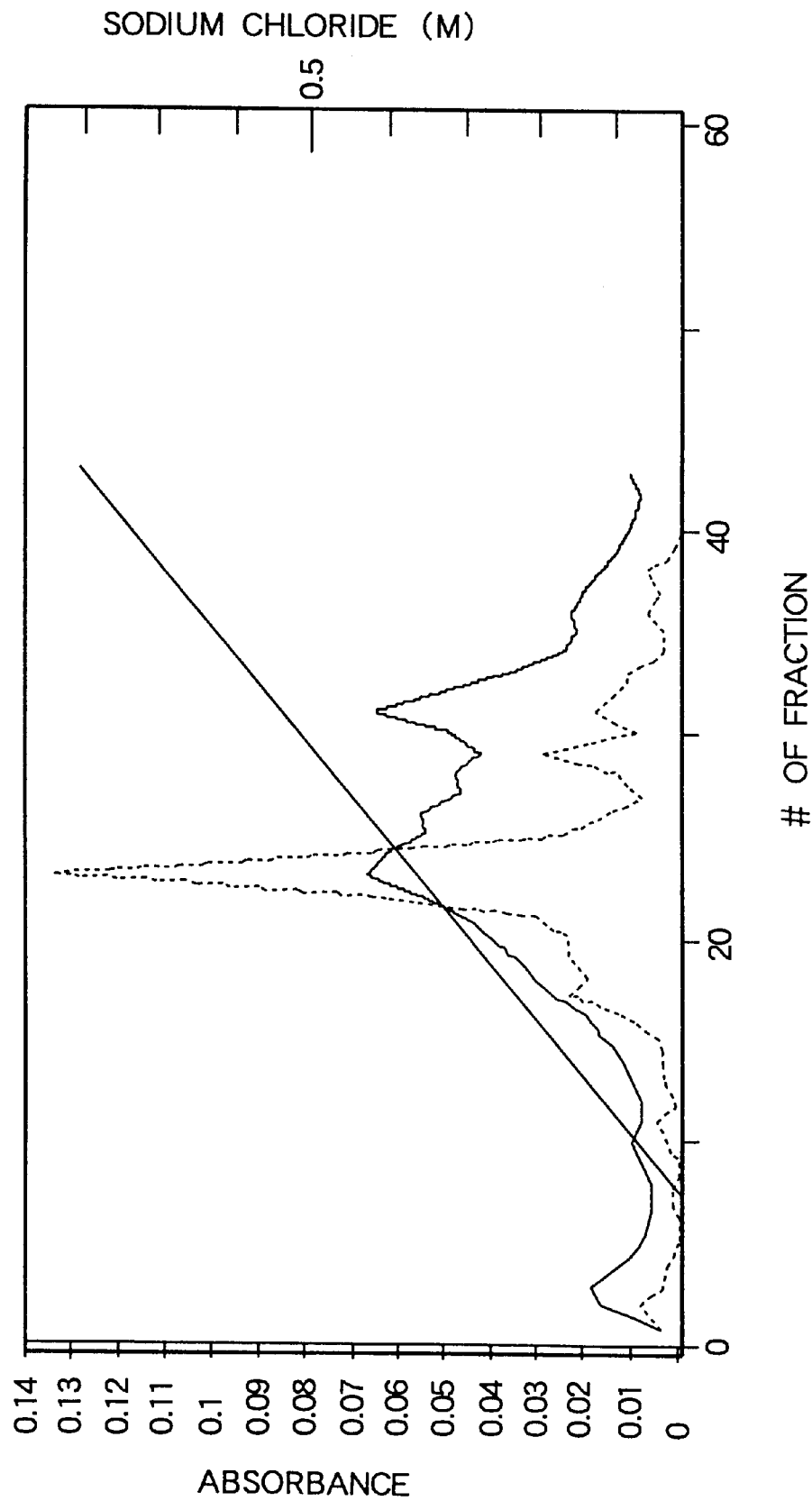
FIG. 3 is a graph showing an elution curve of the nacrein proteins in the sample to be ion-exchanged obtained by DEAE-Sephacel Column Chromatography.
Figure 4:
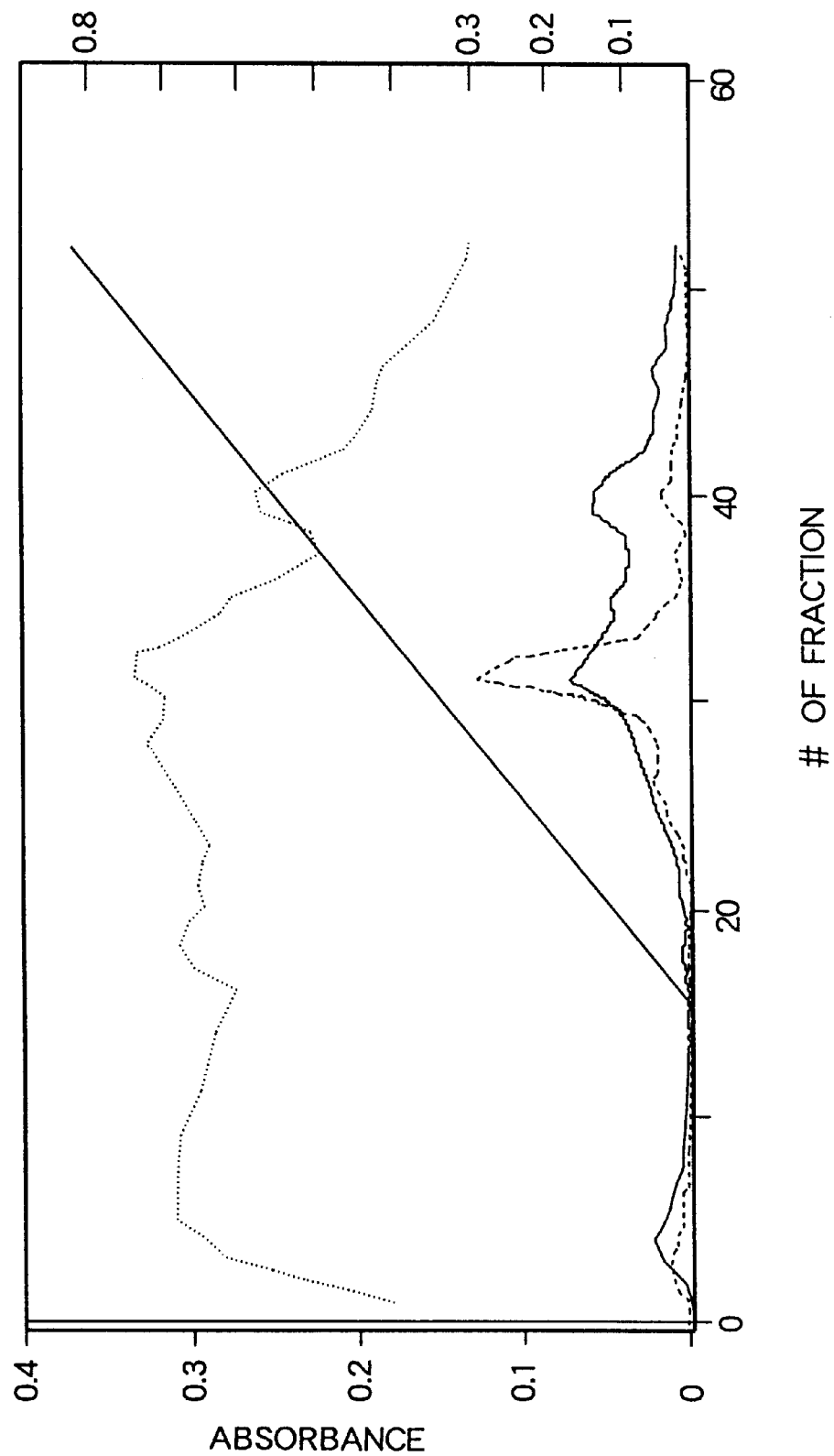
FIG. 4 is a graph showing an absorbance utilizing Stains-all on the eluted fractions referred to in FIG. 3.

On the other hand, similar chromatography was also performed on 4.5 ml of the remaining sample. In the chromatography, similar extraction curve (FIG. 3) like that referred to in FIG. 2 was observed, and an adsorbence pattern ($\mu$=570 nm) with Stains-all on each extacted fraction is shown in FIG. 4 as the dot line.

Further, SDS-PAGE (8~16% gradient) on the fractions 31 and 40 were performed. These fractions are corresponding to an absorbence peak by TCA method on the extracts fractions. Samples were then stained with Coomassie Brilliant Blue G-250 (FIG. 5) and Stains-all (FIG. 6).

Figure 5:
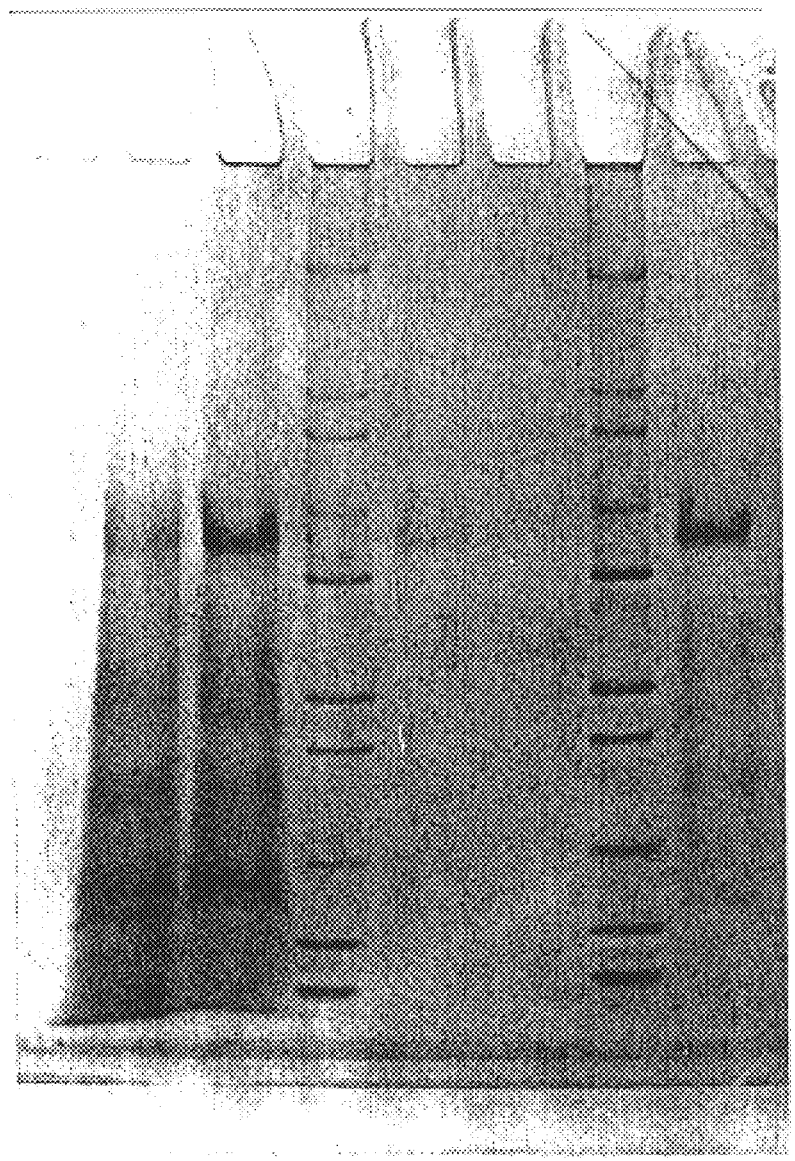
FIG. 5 shows a result obtained by performing SDS-PAGE on the fractions 31 and 40 and staining them with Coomassie Brilliant Blue G-250.
Figure 6:
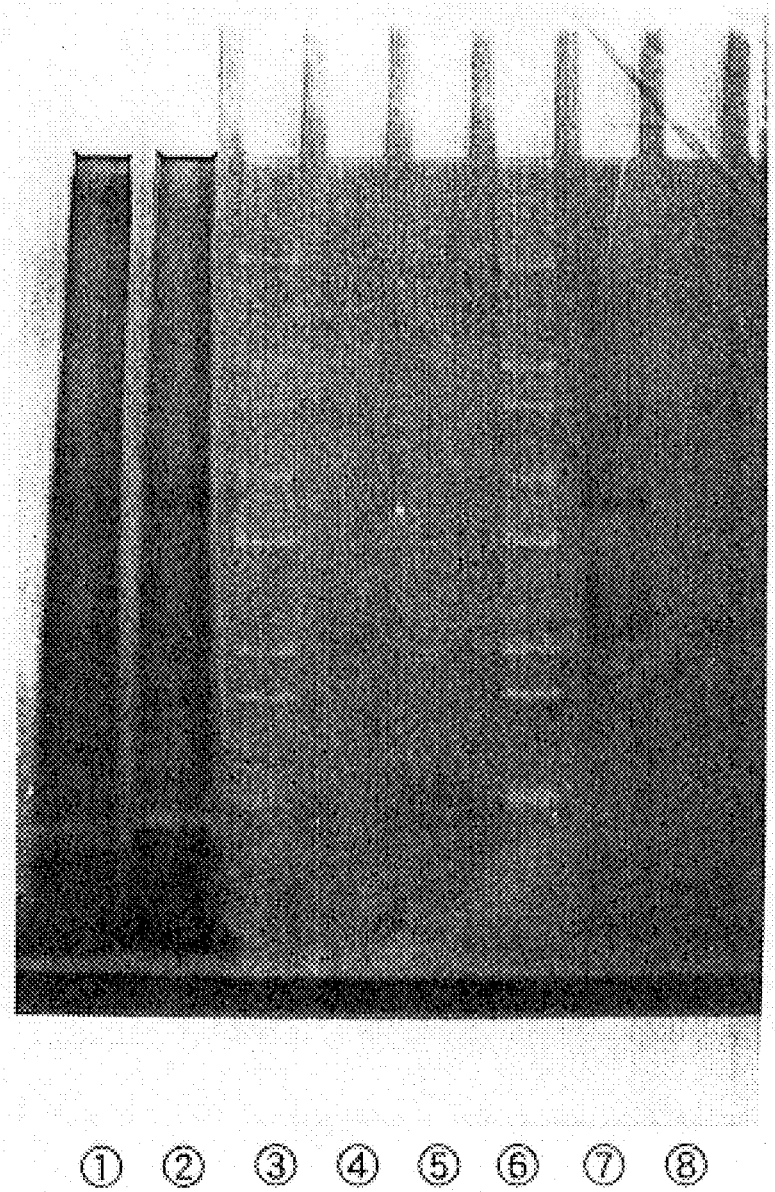
FIG. 6 shows a result obtained by performing SDS-PAGE on the fractions 31 and 40 and staining them with Stains-all.

With reference to FIGS. 5 and 6;

Lane 1 is directed to samples isolated by Drs. Miyashita and Matsushiro (10 $\mu$l)

Lane 2 is directed to samples for the ion-exchange noted above (25 $\mu$l);

Lanes 3 and 6 are directed to the proteins for molecular weight marker [Myosin (Molecular Weight: 200,000), β-galactosidase (Molecular Weight: 116,300), Phosphorylase (Molecular Weight: 97,400), Bovine Serum Albumin (BSA, Molecular Weight: 66,300), Glutamate Dehydrogenase (Molecular Weight: 55,400), Lactate Dehydrogenase (Molecular Weight: 36,500), Carbonic Anhydrase (Molecular Weight: 31,000), Soybean Trypsin Inhibitor (Molecular Weight: 21,500), Lysozyme (Molecular Weight: 14,400), Aprotinin (Molecular Weight: 6,000)];

Lane 4 is the fraction 31 (25 $\mu$l);

Lane 5 is the fraction 40 (25 $\mu$l);

Lane 7 is the ten-times concentrated fraction 31 (25 $\mu$l); and

Lane 8 is the ten-times concentrated fraction 40 (25 $\mu$l).

Based on the results above, the peak fractions 29~33 obtained at the first ion-exchange chromatography and the peak fractions 21~25 obtained at the second ion-exchange chromatography were mixed, and poured the mixture into one dialysis tube (Separation Molecular Weight: 2,000). The mixture was dialyzed overnight at 4° C. together with 10 mM EDTA solution (pH 7.0) as on outer solution. After the dialysis, the samples were adsorbed by DEAE-Sephacel Column in which the inner solution (approximately 100 ml) is equilbrated with 10 mM EDTA. Then, the nacrein protein was directly eluted with 0.8M sodiumchloride (10 mM EDTA) solution. Eluted solution (approximately 10 ml) was concentrated to 2 ml of volume with Ultra Free C-20 (Milipore, Separation Molecular Weight: 10,000) and the concentrated solution was employed as a sample for a gel filtration.

Figure 7:
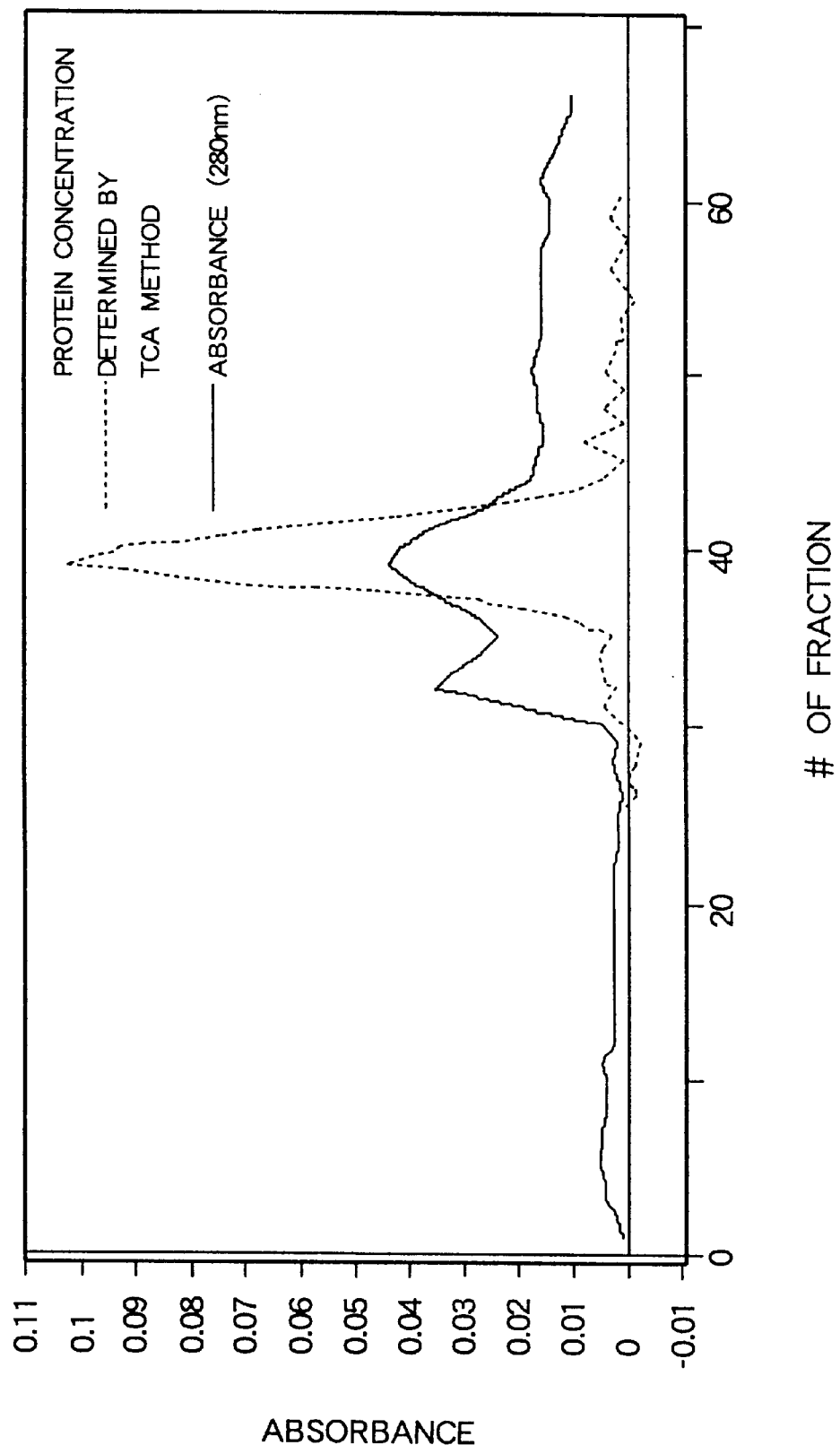
FIG. 7 is a graph showing an elution pattern obtained at G75 gel filtration of the nacrein proteins.

Sephadex G75 was employed for the gel filtration. The sample was added to the G75 Column (Ø20 mm×950 mm) equilbrated with 10 mM EDTA and 0.2M sodium chloride solution (pH 7.0), and was eluted with the same buffer at a flow rate of 12.5 ml/hr. Eluted solution was collected as fractions of 3.5 ml. FIG. 7 is an extraction pattern by G75 gel filtration. In the figure, the solid line is directed to an absorbance at 280 nm wavelength, while the dot line is directed to an absorbance by TCA method at 340 nm wavelength.

Figure 8:
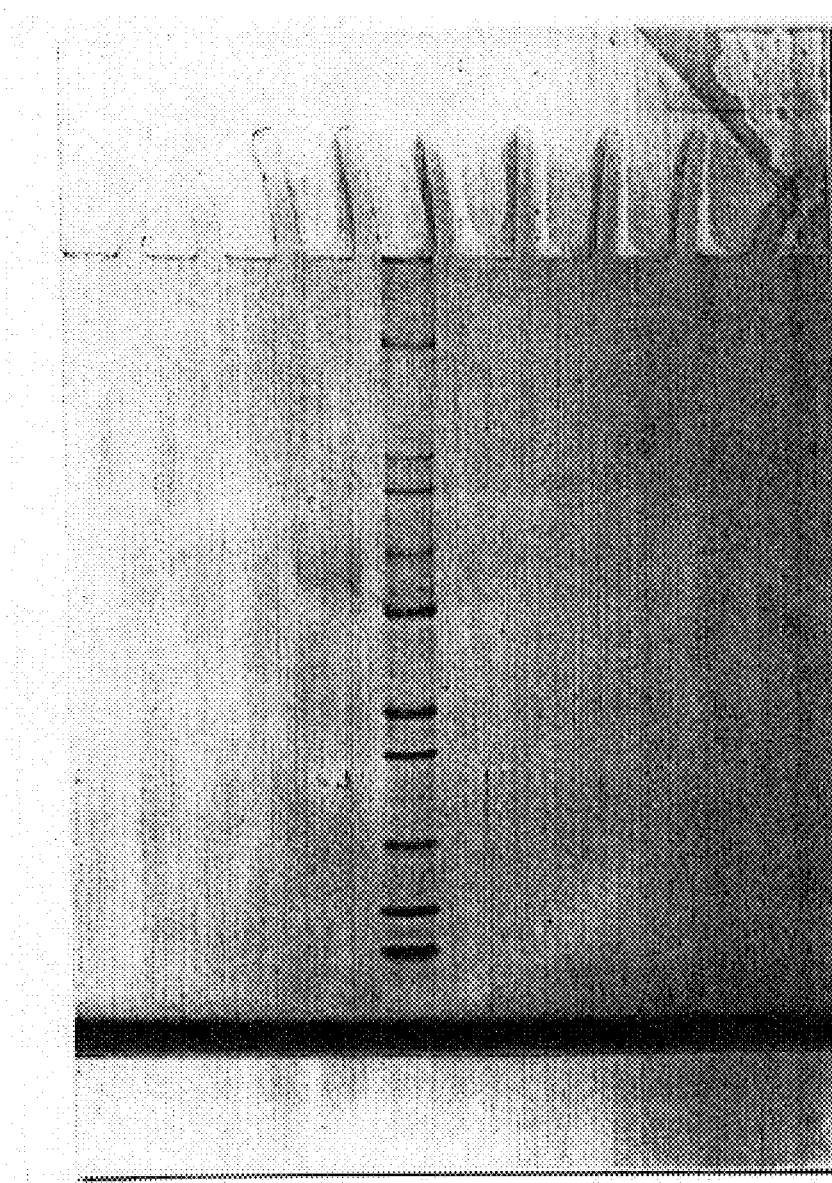
FIG. 8 shows a result of SDS-PAGE on the samples purified by G75 gel filtration.

26 ml of a mixture consisting of peak fractions 37~43 at TCA method fractioned by G75 gel filtration was employed as final purified products. These products form a single band on SDS-PAGE (See, FIG. 8). Then, when the products were quantitated according to TCA method together with BSA as a standard protein, concentration of approximately 20 $\mu$g/ml was confirmed. Accordingly, total purified proteins were calculated at 26×20≈500 $\mu$g. 5 ml of the purified products were concentrated to 0.45 ml with Centricon 10 (Amicon; Separation Molecular Weight=10,000) and the concentrated products were employed as a sample for a N-terminal amino acids sequencing.

③ Discussion

In this purification step, besides minor band like a 37 kD protein, major two protein bands at the molecular weight of approximately 60 kD and 15 kD had been detected in the solution of crude extructs from pearl (See, FIG. 5).

Then, when the crude solution is concentrated and the concentrated solution is applied to a chromatography equipped with an anion-exchange resin DEAE-Sephacel, most of the proteins were gotten in one particular peak. Results of SDS-PAGE on this fraction indicate that this fraction is corresponding to proteins in the molecular weight of approximately 60 kD (See, FIG. 5). Further, because of high stainability with Stains-all thereof, the proteins seems to be $Ca^{2+}$-binding proteins (See, FIG. 6). [K. P. Campbell, D. H. MacLennan & A. O. Jorgensen, "Staining of the $Ca^{2+}$-Binding Proteins, Calsequestrin, Calmodulin, Troponin C, and S-100, with the Cationic Carbocyanin Dye "Stains-all", J. Biol. Chem., 258 (18), pp. 11267–11273 (1983)]. The protein of 60 kD molecular weight also formed a single peak on the gel filtration utilizing Sephadex G75 as a carrier (FIG. 7).

Accordingly, the protein designated as "nacrein" of 60 kD molecular weight is one of the major proteins of the pearl layer and is acid protein (of binding to the anion-exchange resin DEAE Sephacel) with $Ca^{2+}$-binding activity.

On the other hand, although the proteins in the molecular weight of 15 kD is also one of the major protein of the pearl layer, it is basic protein (of not binding to the DEAE Sephacel but passing therethrough) without $Ca^{2+}$-binding activity.

EXAMPLE 2

N-Terminal Amino Acids Sequencing of Nacrein Protein

Foregoing concentrated samples (0.45 ml) were divided into seven lanes to be 25 μl/lane and were applied to SDS-PAGE and an electrophoresis. Then, membrane film containing 60 kD band was excised and was electrically transferred as blotting samples to PVDF membrane filter (Immobilon P).

Then, the transferred membrane was stained with 0.03% Coomassie Brilliant Blue R-250 and the membrane films containing a target band were excised. The films were then set on the blotting sequencer (Type 477A: Applied Biosystems). N-terminal amino acids of the nacrein protein adhered to the films were analyzed twice, and the amino acids sequence was deduced as follows (SEQ ID Nos.:1 and 2).

Ala Ser Met Phe Lys Met Asp Xaa Tyr Met Asp Xaa Gly Xaa Arg(SEQ ID NO:1)

Xaa His Met Phe Lys His Asp His Tyr Met Asp Asp Gly Val Arg-(SEQ ID NO:2)

At the early stage, to deduce the amino acids sequence was difficult, because the final product have not been purified completely and there were differences in the analysis of first and second amino acids in the N-terminal sequence between first and second determination results thereon. But, in view of the other analysis data and facts that nearly all of third through fifteenth amino acids of the N-terminal sequence were coincided between the first and the second determination results, the N-terminal sequence was determined as the following sequence (SEQ ID No.:3).

Ala Ser Met Phe Lys His Asp His Tyr Met Asp Asn Gly Val Arg-(SEQ ID NO:3)

EXAMPLE 3

Cloning of Nacrein cDNA (1) Synthesis of DNA probes corresponding to N-terminal amino acids Base sequence (SEQ ID No.:4) of sense DNA strands was designed with a code table based on amino acids sequence noted above.

44 mer of the following anti-sense DNA strands corresponding to the base sequence is synthesized with DNA synthesizer (No. 392; Applied Biosystems). Alkaline phosphatase is labelled to this probe DNA with DIG oligonucleotide 3'-end labeling kit (Boehringer).

(2) Extraction of mRNA from Mantle Pallial of *Pinctada fucata*

About one hundred *Pinctada fucata* of being cultured were got in Uwazima, Ehime Prefecture, Japan, and several experts excised therefrom the mantle pallial which are just forming the pearl layer. Strips of the excised pallials were then immediately sunk in the phosphorus buffer and were lyophilized instantly with liquid nitrogen. Strips from twenty *Pinctada fucata* were combined and were poured into one polyethylene tube for a centrifugation. After that, the tubes were transported with frozing them by dry ice and have been stored in the deep freezer under the temperature of –80° C.

6M guanidine thiocyanate solution was added (in the proportion of 1:10) to these freezed strips and were crushed with a homogenizer (Polytoron). Whole RNA was extracted from these crushed samples by guanidine-phenol-chloroform method (AGPC method). Approximately 3 mg of RNA was gotten from a single centrifugation tube (including mantle pallial of twenty *Pinctada fucata*). Approximately 20 μg of mRNA was obtained through a purification of poly(A)⁺ mRNA by applying these RNA to an oligo-dT-cellulose column (a purification kit for mRNA: Pharmacia). When these poly(A)⁺ mRNA were applied to an agarose electrophoresis, a band was formed around 18 s.

mRNA obtained from the mantle pallial and applied to the gel electrophoresis was transferred to a nitocellulose filter. Then, when the labelled DNA probes aforenoted were hybridized to the filter, a band indicating positive signal was appeared around 2.3 kb. Such signal had not been detected in the control RNA extracted from the whole body of *Pinctada fucata*. Therefore, it was demonstrated that only RNA sample obtained from the mantle pallial have mRNA of nacrein which can specifically hybridize to the DNA probes.

(3) Construction of cDNA Library cDNA from mRNA obtained from the mantle pallial was prepared with cDNA synthesis kit of Pharmacia. Adapter having EcoRI-NotI site is linked to both ends of synthesized cDNA. cDNA so made was cloned with λgt10 as a vector and was packaged. Then, the plaque was produced thereby in *E. coli* Hf1·NM514 strain. As a result, approximately 270,000 pfu phages were obtained from 2 μg of 20 μg mRNA so purified.

The phages were inoculated into plastic dishes of 9 cm diameter to get approximately 10,000 plaques per one dish, and the appeared plaques were transferred to a nitrocellulose filter. Five filters collected from five dishes were plaque hybridized with the labelled probes noted above, then six independent spots indicating positive signal were obtained. Each plaque corresponding to each of these spots was collected, then, screening (selection) on the plaques indicating positive signal was repeatedly purified them.

After multiplication of the purified phage clones in *E. coli* Hf1 NM514 strain, DNA extracted from each of phage clones and NotI digested were applied to a gel electrophoresis.

Since it came to know that cloned target cDNA fragments have one EcoRI restriction site, DNA extracted from each of the clones was digested with NotI. When such NotI digested gel patterns were transferred to nitrocellulose filter and were hybridized with the labelled probes noted above, DNA fragments of 2.3 kb indicated positive signal. Accordingly, it was concluded that these DNA fragments are cDNA of the nacrein.

EXAMPLE 4

Sequencing on Total Base Sequence of Nacrein cDNA

DNA fragments determined in Example 3 as cDNA of nacrein were subcloned into the plasmid pBluescript. Of the six clones, subcloning on four clones were succeeded and were designated respectively as CλN2, CλN5, CλN6 and CλN9. There are common pattern in the restriction map (a map of restriction sites) prepared for these fragments.

Figure 9:
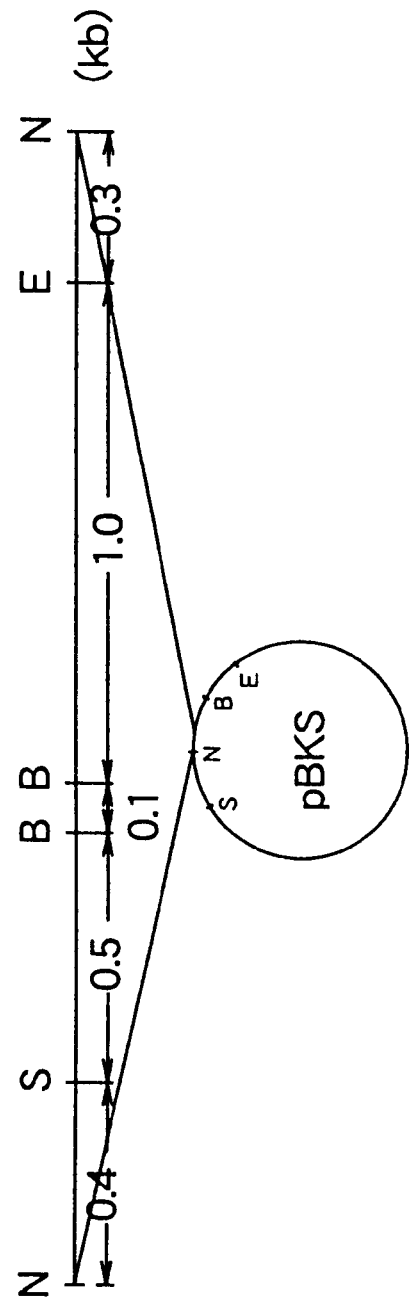
FIG. 9 is a detail of CλN6.

FIG. 9 is a map on CλN6. In FIG. 9, PBKS (Stratagene) is one of the plasmid pBluescript to clone *E. coli,* and points of N, E, B and S denoted in the figure are restriction sites by restriction enzymes NotI, EcoRI, BamHI and SacI respectively.

Since CλN6 illustrated in FIG. 9 could be divided into five fragments, each fragment was subcloned into plasmid pUC19 for the base sequence determination. Since SacI-EcoRI fragments (1.6 kb) without restricting by BamHI are too long to directly sequence it, some deletion strains thereof were prepared by subcloning these fragments into pUC19 and deleting the same, little by little, with Exo III and Bal 31 nuclease. All of these fragments were applied to DNA sequencer (No.373S: Applied Biosystems) to analyze the base sequences, then the total base sequence and the amino acids sequence (SEQ ID No.: 6) in the DNA fragments inserted into CλN6 were determined with software for processing gene information (GENETYX-MAC) by arranging and analyzing data so obtained.

The following facts are clarified through a study of the total base sequence and the amino acids sequence set out in SEQ ID No.: 6.

(1) Coding region is consisting of 447 amino acids (1341 bases) started from methionine [1st amino acid] of 22nd~24th bases and ended at lysine [447th amino acid] of 1360th~1362th bases. Base sequences corresponding to this coding region is set out in SEQ ID No.: 7, while amino acids sequence corresponding to the mature nacrein proteins (coding region without the signal peptide) is set out in SEQ ID No.: 8.

(2) Non-Coding region is positioned from TAG (amber nonsense codon) of 1363rd~1365th bases and contains much bases of AT.

(3) Signal sequence. A sequence is started from methionine [1st amino acid] coded by ATG of 22nd~24th bases and ended at glycine [17th amino acid] coded by GGC of 70th~72nd bases. This sequence is ended with glycine and contains a cluster of hydrophobic amino acids together with that of hydrophilic amino acids subsequent thereto. This portion therefore seems to be a signal sequence of this protein.

(4) Sense strands (SEQ ID No.:4) corresponding to 44 mer DNA probes (SEQ ID No.:5) and synthesized to get the cDNA clone are positioned between G (glycine) of 73th base and G (glycine) of 117th base in SEQ ID No.:6.

(5) Nacrein is $Ca^{2+}$-binding protein. In general, Gly-Asx surrounded by hydrophobic amino acids, so called EF hand structure, have been known as $Ca^{2+}$-binding sites. As a similar structure, 242nd~323rd amino acids sequence corresponding to 745th~990th bases of SEQ ID No.:6 is a quite unique sequence and have 27 repeat units of Gly-Asx-Asn- (Asx; Asp or Asn) sequence (SEQ ID No.:9). This is a surprising discovery.

(6) Sequence search was conducted in data base on amino acids sequence for the proteins (Swissprot protein data base). The results indicated that nacrein have homology with the carbonic anhydrase (hereinafter referred to as "CA"), in particular, with CAII of human erythrocyte (See, FIG. 10). The carbonic anhydrase catalyze a chemical reaction to be processed along with the following formula [I].

$$CO_2 + H_2O \leftrightarrows HCO_3^- + H^+ \qquad [I]$$

Then, the presence of enzymatic activity on nacrein protein was determined in accordance with the following procedures.

Necessary time (T) to reach at pH 7.3 was seen by adding 2 ml of water saturated with carbon dioxide to 3 ml of 20 mM Veronal buffer (pH 8.3) under the presence of 10 μl of the proteins (enzymes) with continuous agitation. Chemical reaction was processed at the temperature of 0° C., because the reaction rate is too large at room temperature. Further, control time ($T_0$) to reach at pH 7.3 without an enzyme was also seen.

Activity of the enzyme will be derived according to the following formula [II] by putting T and To thereinto.

$$\text{Activity (unit)} = (T_0 - T)/T \qquad [II]$$

Results obtained along with aforenoted procedures are shown in the following Table 1.

TABLE 1

DETERMINATION ON CARBONIC ANHYDRASE ACTIVITY

| Sample | Amount (μg) | T (sec.) | Specific Activity (Unit/mg) |
|---|---|---|---|
| — | — | 105 (=$T_0$) | — |
| BECA | 0.1 | 30 | $2.5 \times 10^4$ |
| BECA (heat-inactivated) | 0.1 | 130 | — |
| Nacrein | 0.8 | 45 | $1.6 \times 10^3$ |
| Nacrein | 1.6 | 24 | $2.1 \times 10^3$ |

TABLE 1-continued

DETERMINATION ON CARBONIC ANHYDRASE ACTIVITY

| Sample | Amount (μg) | T (sec.) | Specific Activity (Unit/mg) |
|---|---|---|---|
| Nacrein (heat-inactivated) | 0.8 | 140 | — |
| BSA | 4.0 | 120 | — |

BECA: Bovine Erythrocyte Carbonic Anhydrase
BSA: Bovine Serum Albumin

Data listed in Table is an average of two individual experiments.

Apparently from the results shown in Table 1, the nacrein is an enzyme protein having an activity of carbonic anhydrase.

In light of the results noted above, nacrein is the structural element of the pearl layer and is also the functional protein which can synthesize aragonite crystal of the calcium carbonate from $Ca^{2+}$ and carbonate ion respectively dissolved in the sea water.

(7) This protein may have molecular weight of 50,000, if it is calculated based on the molecular weight of amino acids in the coding region without the signal sequence. There is difference of about 10,000 in molecular weight between the calculated weight and that of about 60,000 determined by mobility at SDS-PAGE.

EXAMPLE 5

Expression of Nacrein in Host [E. coli]

Since the base sequence of nacrein cDNA were determined in the previous Example, gene expression of such cDNA was tried in the cell of E. coli with a vector having the cDNA linked thereto.

Figure 11:
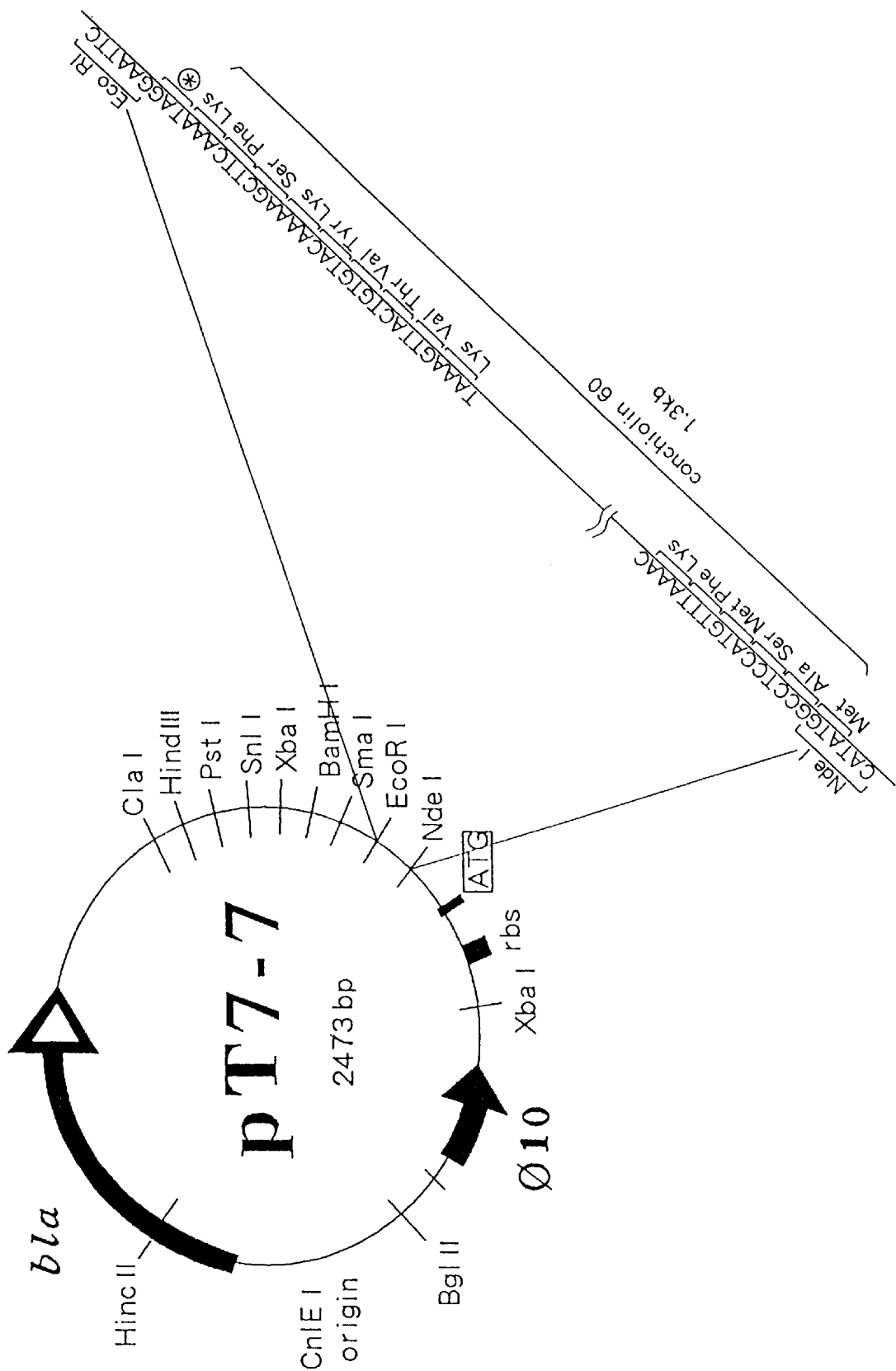
FIG. 11 illustrates an insertion of an open reading frame of the nacrein cDNA into NdeI-EcoRI site of the plasmid pT7-7.

First of all, pT7-7 [Studier, F. W. et al., Methods Enzymol. 185, 60–89 (1991)] was selected as a vector for the gene expression. Then, PCR-amplified open reading frame of the nacrein was inserted at NdeI-EcoRI site as shown in FIG. 11.

Apparently from the structure of the vector so constructed, expression of the inserted gene is controlled by promoter Ø10 to be functioned with T7RNA polymerase positioned prior to the gene. On the other hand, since expression of T7RNA polymerase can be induced in E. coli BL21 (λDE3) strain by an addition of IPTG (isopropylthiogalactoside), the synthesis of the nacrein was studied by preparing transformants of this strain transformed with the plasmid noted above.

An anti-rabitt-nacrein-antibody was used to detect and determined the quantity of the nacrein. The antibody is an anti-serum produced by preparing an unit preparation for injection consisting of a mixture (an antigen) of equal volume of 1 ml of nacrein sample (20 μg/ml protein) purified according to the Example 1 and an adjuvant (Wako Junyaku), immunizing twice rabbits with the unit preparation every 3 weeks, and collecting blood on one month after then. The antibody can detect the nacrein even if it is diluted to 1/10,000.

Transformed bacterial cells, which were induced by IPTG and thereby synthesized the nacrein, was solved by SDS. All of the solved bacterium were applied to SDS-electrophoresis, and were transferred to PVDF membrane filter (Immobilon P) with a blotting divice (Nihon-Eido Co., Ltd.).

Then the sample were washed with anti-babbit-serum, then with goat-anti-rabbit IgG antibody labelled with peroxidase of horse radish, and color was developed with DAB (3,3'-diaminobenzidine).

Figure 12:
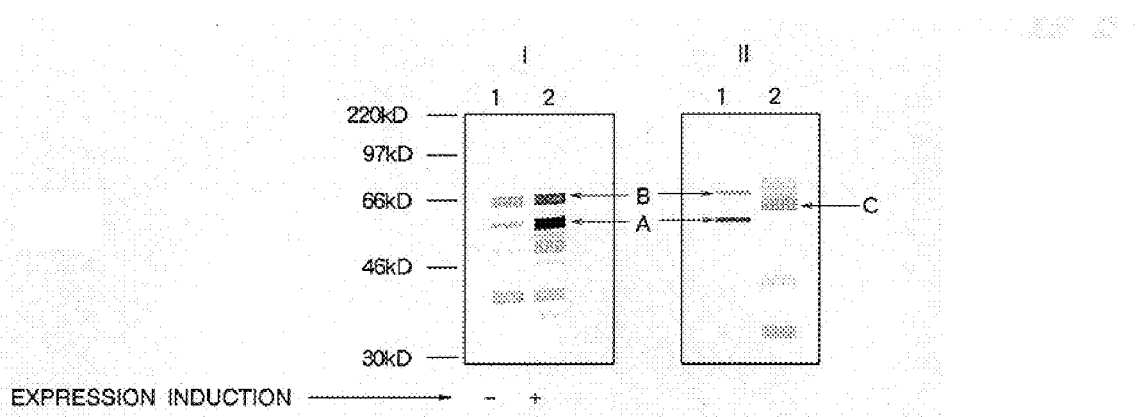
FIG. 12 shows a result of SDS-electrophoresis conducted on the nacrein proteins expressed in *E. coli* with a genetic engineering technique.

With respect to each of the isolated strains, positive spots having the reactivity with the antibody in the control lane (−) without IPTG were not detected. In contrast thereto, dark black band was clearly detected in the experimental lane (+) induced with IPTG (FIG. 12-I).

These results suggest that the nacrein proteins (several percent of the total proteins deduced from the other data on stainability with Coomassie Blue) would be produced in the cell of E. coli. These proteins may be biosynthesized in the cell of yeast or silkworm according to the same procedure. If the industrial production thereof is planned, it will be considered as to which system is the most preferable to effectively synthesize natural-like proteins and is advantageous to the purification of the products.

When the biosynthesized nacrein (Band A) of this Example and the natural nacrein (Example 1: Band C) are applied to electriphoresis and are compared (FIG. 12-II), molecular weight of the natural nacrein is apparently larger than that of the biosynthesized nacrein. This may due to a modification after the translation. In view of the thesis [Tetsuro Samata: Venus 47, 127–140 (1988)] suggesting that these proteins may glycoprotein, although PAS-staining had been performed to see the presence of the glycosaccharides and restriction by N-glucosidase, an expected result could not be obtained. Besides the molecular weight, there was considerable difference on pI between the proteins biosynthesized in E. coli and the natural nacrein proteins. Further, in light of the difference on stainability by Stains-all (an indicator of $Ca^{2+}$-binding activity), acid groups have been bonded thereto by β-carboxylating asparatic acids in the repeated region of sequence of Gly-Asx-Asn (SEQ ID NO:9). Therefore, pI of the natural nacrein molecule and $Ca^{2+}$-binding activity comes to be larger.

Taking such conditions into the consideration, to realize the large scale production of the nacrein molecule similar to the natural nacrein, it would be necessary that the nacrein cDNA was introduced in the eucaryotic host like yeast or silkworm and was expressed therein.

INDUSTRIAL APPLICABILITY

As stated above, according to the present invention, prior producing technique depended on the environmental conditions may be unnecessary, and pearl proteins can be produced artificially. Further, desirous effects, like an industrial mass production of the pearl, can also be expected by utilizing the gene structure analayzed by the inventor which is involving in a formation of pearl proteins.

I claim:

1. An isolated DNA molecule encoding a nacrein pearl protein, wherein said DNA molecule comprises the base sequence depicted SEQ ID NO:7.

2. The DNA molecule of to claim 1, wherein said protein is nacrein protein produced by *Pinctada fucata*.

3. The DNA molecule of to claim 2, wherein the molecular weight of said nacrein protein is 60,000 as determined by SDS-PAGE.

4. An isolated nacrein protein derived from a pearl, wherein said protein comprises the amino acid sequence depicted in SEQ ID NO:8.

5. The protein of claim 4, wherein said protein is nacrein protein produced by *Pinctada fucata*.

6. The protein of claim 4 or 5, wherein said amino acid sequence is encoded by the base sequence depicted in SEQ ID NO:7.

7. The protein of claim 4 or 5 wherein the molecular weight of said nacrein protein is 60,000 as determined by SDS-PAGE.

8. A method for isolating nacrein protein derived from *Pinctada fucata*, said method comprising (a) extracting pearl protein from pearl layer of *Pinctada fucata*;

(b) collecting fractions containing the protein in the molecular weight of 60,000 as determined by applying the pearl protein to SDS-PAGE;

(c) synthesizing probes encoding N-terminal amino acids sequence of said pearl protein;

(d) cloning cDNA to be hybridized with said probes from cDNA library constructed based on mRNA obtained from mantle of *Pinctada fucata*; and (e) expressing nacrein proteins by introducing said cDNA into a host cell like *Escherichia coli*.

9. Method according to claim 8, wherein said host is a cell of an organism selected from the group consisting of *Escherichia coli*, yeast and silkworm.

10. Method according to claim 9, wherein said host is a cell of *Escherichia coli* BL21(λDE3).

11. Protein according to claim 6 wherein the molecular weight of said nacrein protein is 60,000 as determined by SDS-PAGE.

* * * * *

UNITED STATES PATENT AND TRADEMARK OFFICE
CERTIFICATE OF CORRECTION

PATENT NO.    :   5,968,772
DATED         :   October 19, 1999
INVENTOR(S)   :   Matsushiro It is certified that error appears in the above-identified patent and that said Letters Patent is hereby corrected as shown below:

<u>In the Claims</u>:

At column 23, line 3 of claim 1, immediately following "depicted" insert --in--.

At column 23, line 1 of claim 2, immediately following "molecule of" delete "to".

At column 23, line 1 of claim 3, immediately following "molecule of" delete "to".

Signed and Sealed this

Seventeenth Day of October, 2000

Q. TODD DICKINSON

*Attest:*

*Attesting Officer*            *Director of Patents and Trademarks*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
          (A) LENGTH: 15 amino acids
          (B) TYPE: amino acid
          (C) STRANDEDNESS: Not Relevant
          (D) TOPOLOGY: linear (ii) MOLECULE TYPE: peptide (xi) SEQUENCE DESCRIPTION: SEQ ID NO:1:

Ala Ser Met Phe Lys Met Asp Xaa Tyr Met Asp Xaa Gly Xaa Arg
1               5                   10                  15

(2) INFORMATION FOR SEQ ID NO:2:

(i) SEQUENCE CHARACTERISTICS:
          (A) LENGTH: 15 amino acids
          (B) TYPE: amino acid
          (C) STRANDEDNESS: Not Relevant
          (D) TOPOLOGY: linear (ii) MOLECULE TYPE: peptide (ix) FEATURE:
          (A) NAME/KEY: misc_feature
          (B) LOCATION: 1
          (D) OTHER INFORMATION: /note= "Amino Acid of this position
               is Ser, Ala, or Gly"

(ix) FEATURE:
          (A) NAME/KEY: misc_feature
          (B) LOCATION: 8
          (D) OTHER INFORMATION: /note= "Amino Acid of this position
               is His or Asp"

(xi) SEQUENCE DESCRIPTION: SEQ ID NO:2:

Xaa His Met Phe Lys His Asp Xaa Tyr Met Asp Asp Gly Val Arg
1               5                   10                  15

(2) INFORMATION FOR SEQ ID NO:3:

(i) SEQUENCE CHARACTERISTICS:
          (A) LENGTH: 15 amino acids
          (B) TYPE: amino acid
          (C) STRANDEDNESS: Not Relevant
          (D) TOPOLOGY: linear (ii) MOLECULE TYPE: peptide (xi) SEQUENCE DESCRIPTION: SEQ ID NO:3:

Ala Ser Met Phe Lys His Asp His Tyr Met Asp Asn Gly Val Arg
1               5                   10                  15

(2) INFORMATION FOR SEQ ID NO:4:

(i) SEQUENCE CHARACTERISTICS:
          (A) LENGTH: 44 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthesized DNA"

(iv) ANTI-SENSE: NO (xi) SEQUENCE DESCRIPTION: SEQ ID NO:4:

KCNCAYATGT TYAARMWBGA YSAYTAYATG GAYGAYGGNG TNMG     44

(2) INFORMATION FOR SEQ ID NO:5:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthesized DNA"

(iv) ANTI-SENSE: YES (ix) FEATURE:
        (A) NAME/KEY: misc_feature
        (B) LOCATION: 42
        (D) OTHER INFORMATION: /note= "N = INOSINE"

(xi) SEQUENCE DESCRIPTION: SEQ ID NO:5:

CKNACNCCRT CRTCCATRTA RTSRTCVWKY TTRAACATRT GNSW     44

(2) INFORMATION FOR SEQ ID NO:6:

(i) SEQUENCE CHARACTERISTICS:
        (A) LENGTH: 2363 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 22..1362

(ix) FEATURE:
        (A) NAME/KEY: sig_peptide
        (B) LOCATION: 22..72

(ix) FEATURE:
        (A) NAME/KEY: binding site
        (B) LOCATION: 73..120

(ix) FEATURE:
        (A) NAME/KEY: repeat_region
        (B) LOCATION: 745..990

(ix) FEATURE:
        (A) NAME/KEY: repeat_unit
        (B) LOCATION: 745..748

(ix) FEATURE:
        (A) NAME/KEY: active site
        (B) LOCATION: 1144..1287

(xi) SEQUENCE DESCRIPTION: SEQ ID NO:6:

```
TAGTAAATGT GAAGATTGGT G ATG TAT CTT CAT TTG ACT GCC CTA TGT GTT      51
                       Met Tyr Leu His Leu Thr Ala Leu Cys Val
                        1               5                  10

GTT ATT CCG CTG TGT TAT GGC GCC TCC ATG TTT AAA CAT GAC CAC TAC      99
Val Ile Pro Leu Cys Tyr Gly Ala Ser Met Phe Lys His Asp His Tyr
         15                  20                  25

ATG GAC AAT GGT GTG AGG TAT CCT AAT GGT GAC GGA ATC TGT AAA CAA     147
Met Asp Asn Gly Val Arg Tyr Pro Asn Gly Asp Gly Ile Cys Lys Gln
             30                  35                  40

TTG AAT GAA ACC AAA TGT GAT GCA GGG TTT AGC TAT GAT AGG AGT ATA     195
Leu Asn Glu Thr Lys Cys Asp Ala Gly Phe Ser Tyr Asp Arg Ser Ile
         45                  50                  55
```

```
TGT GAA GGT CCT CAT TAT TGG CAC ACC ATA TCG AAA TGC TTC ATT GCA      243
Cys Glu Gly Pro His Tyr Trp His Thr Ile Ser Lys Cys Phe Ile Ala
    60                  65                  70

TGT GGA ATT GGA CAG AGA CAA TCT CCA ATC AAC ATC GTT TCT TAT GAT      291
Cys Gly Ile Gly Gln Arg Gln Ser Pro Ile Asn Ile Val Ser Tyr Asp
75                  80                  85                  90

GCT AAA TTT CGT CAG CGT TTG CCA AAA TTG AAA TTC AAG CCA CAT ATG      339
Ala Lys Phe Arg Gln Arg Leu Pro Lys Leu Lys Phe Lys Pro His Met
                95                  100                 105

GAG AAA TTA AAA ACA GAA GTG ACC AAT CAT CAG AAC CGA GCT CCA GAG      387
Glu Lys Leu Lys Thr Glu Val Thr Asn His Gln Asn Arg Ala Pro Glu
            110                 115                 120

TTC GAG CCA GAG GAT GGG GAA AAT CTG TAC GTG AAG CTA AAT AAC CTA      435
Phe Glu Pro Glu Asp Gly Glu Asn Leu Tyr Val Lys Leu Asn Asn Leu
        125                 130                 135

GTG GAC GGT CAT TAT AAA TTC CAT AAT CTT CAC GTT CAT AAT GGT AGA      483
Val Asp Gly His Tyr Lys Phe His Asn Leu His Val His Asn Gly Arg
    140                 145                 150

ACC AGA CGT AAG GGA TCA GAA CAC AGT GTT AAC GGT CGT TTC ACA CCT      531
Thr Arg Arg Lys Gly Ser Glu His Ser Val Asn Gly Arg Phe Thr Pro
155                 160                 165                 170

ATG GAG GCT CAT TTG GTT TTC CAT CAT GAT GAT CAA ACA CAC TTT GAA      579
Met Glu Ala His Leu Val Phe His His Asp Asp Gln Thr His Phe Glu
                175                 180                 185

CCT ACA CGC ACT AAG CTG GGA GGA GCA TTC CCT GGT CAT AAC GAT TTT      627
Pro Thr Arg Thr Lys Leu Gly Gly Ala Phe Pro Gly His Asn Asp Phe
            190                 195                 200

GTC GTC GTT GGA GTT TTT CTT GAG GTC GGA GAT GAC GGC TTT GGC GAC      675
Val Val Val Gly Val Phe Leu Glu Val Gly Asp Asp Gly Phe Gly Asp
        205                 210                 215

GAA CCG GAT GAC GAA GAA TGT AAA CAC ATC TTA AAG GGA CAT CAC CCT      723
Glu Pro Asp Asp Glu Glu Cys Lys His Ile Leu Lys Gly His His Pro
    220                 225                 230

GAT AAT AAC GAG AAC GGC AAT GGA GAC AAT GGC AAT AAC GGC TAC AAT      771
Asp Asn Asn Glu Asn Gly Asn Gly Asp Asn Gly Asn Asn Gly Tyr Asn
235                 240                 245                 250

GGG GAC AAC GGT AAC AAT GGT GAC AAC GGC AAT AAC AGC TAC AAT GGG      819
Gly Asp Asn Gly Asn Asn Gly Asp Asn Gly Asn Asn Ser Tyr Asn Gly
                255                 260                 265

GAC AAC GGT AAC AAT GGT GTC AAC GGC AAT AAC GGC TAC AAT GGG GAC      867
Asp Asn Gly Asn Asn Gly Val Asn Gly Asn Asn Gly Tyr Asn Gly Asp
            270                 275                 280

AAC GGT AAC AAT GGA GAC AAC GGC AAT AAC GGC TAC AAT GGG GAC AAC      915
Asn Gly Asn Asn Gly Asp Asn Gly Asn Asn Gly Tyr Asn Gly Asp Asn
        285                 290                 295

GGT AAC AAT GGT GAC AAC GGC AAT AAC GGT GAA AAC GGC AAT AAC GGT      963
Gly Asn Asn Gly Asp Asn Gly Asn Asn Gly Glu Asn Gly Asn Asn Gly
    300                 305                 310

GAA AAC GGC AAT AAC GGT GAA AAT GGT CAC AAA CAC GGA TGT CGG GTA     1011
Glu Asn Gly Asn Asn Gly Glu Asn Gly His Lys His Gly Cys Arg Val
315                 320                 325                 330

AAG AAA GCA AAG CAT CTC AGT AGG ATC CTG GAA TGT GCT TAT AGA AAC     1059
Lys Lys Ala Lys His Leu Ser Arg Ile Leu Glu Cys Ala Tyr Arg Asn
                335                 340                 345

GAT AAG GTC AGA GAG TTC AAG AAA GTT GGA GAA GAG GAA GGG TTA GAT     1107
Asp Lys Val Arg Glu Phe Lys Lys Val Gly Glu Glu Glu Gly Leu Asp
            350                 355                 360

GTT CAT CTA ACA CCG GAG ATG GCT TTG CCG CCA CTG AAG TAC AGA CAT     1155
Val His Leu Thr Pro Glu Met Ala Leu Pro Pro Leu Lys Tyr Arg His
        365                 370                 375
```

-continued

```
TAC TAT ACA TAC GAG GGA TCC CTG ACC ACT CCC CCG TGT ACA GAG TCT        1203
Tyr Tyr Thr Tyr Glu Gly Ser Leu Thr Thr Pro Pro Cys Thr Glu Ser
    380                 385                 390

GTC CTC TGG GTT GTT CAA AAA TGC CAT GTG CAG GTG TCA AGA AGG GTT        1251
Val Leu Trp Val Val Gln Lys Cys His Val Gln Val Ser Arg Arg Val
395                 400                 405                 410

CTT CAT GCA TTA CGA AAT GTT GAA GGA TAT AAA GAT GGT ACC ACA CTA        1299
Leu His Ala Leu Arg Asn Val Glu Gly Tyr Lys Asp Gly Thr Thr Leu
                415                 420                 425

AGA AAG TAT GGA ACT AGA CGT CCA ACG CAA AAG AAT AAA GTT ACT GTG        1347
Arg Lys Tyr Gly Thr Arg Arg Pro Thr Gln Lys Asn Lys Val Thr Val
            430                 435                 440

TAC AAA AGC TTC AAA TAGTTGACAT AGTTTTTGTT CTTTTCCTTA TAGAGACATG        1402
Tyr Lys Ser Phe Lys
            445

TAACACAGCC AATTATGTTT CATATGTAAT CCATGTAAAA TACAGGATCT TTACATAAAT     1462

ATTCATGTGA AACAAGCACG AACATTAAAG GACTAGGTGC GCTAACCCCT TATATCGGCC     1522

CTATAATTTC GACGAGAAAT GCTTTTAATA AACAAACTAT TAATTATAGC TTTTTGCAAT     1582

GTTGAATGTT TGAGAAAATA CCGCATCATA TTTTTTAGCC CTCGTAACGT CACGCGAGTG     1642

ATGTATGATG TCATGTTCTG AAAGTCATTT GCCCTGAATG ACGCAAAACA AATGAGAATC     1702

ATCGTATTTT ACATACAAAT CTTCAAATTC ATCTGCGATT CAGGCCTCGA ACACGATATT     1762

TTTTATGCAA ATTTAAAGGC CGATCAAAAA TCCATCGATT AGTACAAATA TTATCGTGGG     1822

CAATTAAGGC CTGGAACGAT ACTTAATTTC ATAAATTTTA ATCGAAATTT CGCTGATTTA     1882

TTGATATTTT CAATGAGTTT CAACGTTTTA GACATTTTTT TGTAATATTC AGTATAGGAC     1942

TATGAAATCA AAAAAGCTT TCCTGATATG GATTCACCAT ACATTTAACA TTTCAAAAAC     2002

TAGAATATTA TGGATATATG AACAACTTTG AAAATGGGGC CGATATGGCA GGTTACCGAA     2062

CCTACTTCTT TTTATCAAAT TTTTTACATG AAATTCATGG GAAGTTTCCG ACATCAATTT     2122

CATGTGAATT CTATATCGCA TGAAGGTCAC AAAGAAAATT TCATGTAAAA TTCATGCGAA     2182

GGAAATTCAT GTGAAACTCA TGTGAAATAT TTTTCACATA AATCTTAAGT GAAAAGTATA     2242

TAAATTTCAC AACTTTCATG TGAAATTTAA GTGATGCTCA TTTTGTATGG ATTTCATGTG     2302

AGGCATAATT GACTGCTTGT ACTATGTAAT TAGAACAAAA TGTCAAATAT TTAATAAATG     2362

A                                                                    2363
```

(2) INFORMATION FOR SEQ ID NO:7:

(i) SEQUENCE CHARACTERISTICS:
        (A) LENGTH: 1341 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: sig_peptide
        (B) LOCATION: 21..51

(ix) FEATURE:
        (A) NAME/KEY: binding site
        (B) LOCATION: 52..99

(ix) FEATURE:
        (A) NAME/KEY: repeat_region
        (B) LOCATION: 742..969

(ix) FEATURE:
        (A) NAME/KEY: repeat_unit (B) LOCATION: 724..727

(ix) FEATURE:
     (A) NAME/KEY: active site
     (B) LOCATION: 1123..1266

(xi) SEQUENCE DESCRIPTION: SEQ ID NO:7:

| | | | | | |
|---|---|---|---|---|---|
| ATGTATCTTC | ATTTGACTGC | CTATGTGTT | GTTATTCCGC | TGTGTTATGG | CGCCTCCATG | 60 |
| TTTAAACATG | ACCACTACAT | GGACAATGGT | GTGAGGTATC | CTAATGGTGA | CGGAATCTGT | 120 |
| AAACAATTGA | ATGAAACCAA | ATGTGATGCA | GGGTTTAGCT | ATGATAGGAG | TATATGTGAA | 180 |
| GGTCCTCATT | ATTGGCACAC | CATATCGAAA | TGCTTCATTG | CATGTGGAAT | TGGACAGAGA | 240 |
| CAATCTCCAA | TCAACATCGT | TTCTTATGAT | GCTAAATTTC | GTCAGCGTTT | GCCAAAATTG | 300 |
| AAATTCAAGC | CACATATGGA | GAAATTAAAA | ACAGAAGTGA | CCAATCATCA | GAACCGAGCT | 360 |
| CCAGAGTTCG | AGCCAGAGGA | TGGGGAAAAT | CTGTACGTGA | AGCTAAATAA | CCTAGTGGAC | 420 |
| GGTCATTATA | AATTCCATAA | TCTTCACGTT | CATAATGGTA | GAACCAGACG | TAAGGGATCA | 480 |
| GAACACAGTG | TTAACGGTCG | TTTCACACCT | ATGGAGGCTC | ATTTGGTTTT | CCATCATGAT | 540 |
| GATCAAACAC | ACTTTGAACC | TACACGCACT | AAGCTGGGAG | GAGCATTCCC | TGGTCATAAC | 600 |
| GATTTTGTCG | TCGTTGGAGT | TTTTCTTGAG | GTCGGAGATG | ACGGCTTTGG | CGACGAACCG | 660 |
| GATGACGAAG | AATGTAAACA | CATCTTAAAG | GGACATCACC | CTGATAATAA | CGAGAACGGC | 720 |
| AATGGAGACA | ATGGCAATAA | CGGCTACAAT | GGGGACAACG | GTAACAATGG | TGACAACGGC | 780 |
| AATAACAGCT | ACAATGGGGA | CAACGGTAAC | AATGGTGTCA | ACGGCAATAA | CGGCTACAAT | 840 |
| GGGGACAACG | GTAACAATGG | AGACAACGGC | AATAACGGCT | ACAATGGGGA | CAACGGTAAC | 900 |
| AATGGTGACA | ACGGCAATAA | CGGTGAAAAC | GGCAATAACG | GTGAAAACGG | CAATAACGGT | 960 |
| GAAAATGGTC | ACAAACACGG | ATGTCGGGTA | AGAAAGCAA | AGCATCTCAG | TAGGATCCTG | 1020 |
| GAATGTGCTT | ATAGAAACGA | TAAGGTCAGA | GAGTTCAAGA | AAGTTGGAGA | AGAGGAAGGG | 1080 |
| TTAGATGTTC | ATCTAACACC | GGAGATGGCT | TTGCCGCCAC | TGAAGTACAG | ACATTACTAT | 1140 |
| ACATACGAGG | GATCCCTGAC | CACTCCCCCG | TGTACAGAGT | CTGTCCTCTG | GGTTGTTCAA | 1200 |
| AAATGCCATG | TGCAGGTGTC | AAGAAGGGTT | CTTCATGCAT | TACGAAATGT | TGAAGGATAT | 1260 |
| AAAGATGGTA | CCACACTAAG | AAAGTATGGA | ACTAGACGTC | AACGCAAAA | GAATAAAGTT | 1320 |
| ACTGTGTACA | AAAGCTTCAA | A | | | | 1341 |

(2) INFORMATION FOR SEQ ID NO:8:

(i) SEQUENCE CHARACTERISTICS:
      (A) LENGTH: 430 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:8:

```
Ala Ser Met Phe Lys His Asp His Tyr Met Asp Asn Gly Val Arg Tyr
 1               5                  10                  15

Pro Asn Gly Asp Gly Ile Cys Lys Gln Leu Asn Glu Thr Lys Cys Asp
            20                  25                  30

Ala Gly Phe Ser Tyr Asp Arg Ser Ile Cys Glu Gly Pro His Tyr Trp
        35                  40                  45

His Thr Ile Ser Lys Cys Phe Ile Ala Cys Gly Ile Gly Gln Arg Gln
    50                  55                  60

Ser Pro Ile Asn Ile Val Ser Tyr Asp Ala Lys Phe Arg Gln Arg Leu
```

```
                65                  70                  75                  80
Pro Lys Leu Lys Phe Lys Pro His Met Glu Lys Leu Lys Thr Glu Val
                    85                  90                  95

Thr Asn His Gln Asn Arg Ala Pro Glu Phe Glu Pro Glu Asp Gly Glu
                100                 105                 110

Asn Leu Tyr Val Lys Leu Asn Asn Leu Val Asp Gly His Tyr Lys Phe
                115                 120                 125

His Asn Leu His Val His Asn Gly Arg Thr Arg Arg Lys Gly Ser Glu
            130                 135                 140

His Ser Val Asn Gly Arg Phe Thr Pro Met Glu Ala His Leu Val Phe
145                 150                 155                 160

His His Asp Asp Gln Thr His Phe Glu Pro Thr Arg Thr Lys Leu Gly
                165                 170                 175

Gly Ala Phe Pro Gly His Asn Asp Phe Val Val Gly Val Phe Leu
                180                 185                 190

Glu Val Gly Asp Asp Gly Phe Gly Asp Glu Pro Asp Asp Glu Glu Cys
                195                 200                 205

Lys His Ile Leu Lys Gly His His Pro Asp Asn Asn Glu Asn Gly Asn
                210                 215                 220

Gly Asp Asn Gly Asn Asn Gly Tyr Asn Gly Asp Asn Gly Asn Asn Gly
225                 230                 235                 240

Asp Asn Gly Asn Asn Ser Tyr Asn Gly Asp Asn Gly Asn Asn Gly Val
                245                 250                 255

Asn Gly Asn Asn Gly Tyr Asn Gly Asp Asn Gly Asn Asn Gly Asp Asn
                260                 265                 270

Gly Asn Asn Gly Tyr Asn Gly Asp Asn Gly Asn Asn Gly Asp Asn Gly
                275                 280                 285

Asn Asn Gly Glu Asn Gly Asn Asn Gly Glu Asn Gly Asn Asn Gly Glu
                290                 295                 300

Asn Gly His Lys His Gly Cys Arg Val Lys Lys Ala Lys His Leu Ser
305                 310                 315                 320

Arg Ile Leu Glu Cys Ala Tyr Arg Asn Asp Lys Val Arg Glu Phe Lys
                325                 330                 335

Lys Val Gly Glu Glu Glu Gly Leu Asp Val His Leu Thr Pro Glu Met
                340                 345                 350

Ala Leu Pro Pro Leu Lys Tyr Arg His Tyr Tyr Thr Tyr Glu Gly Ser
                355                 360                 365

Leu Thr Thr Pro Pro Cys Thr Glu Ser Val Leu Trp Val Val Gln Lys
                370                 375                 380

Cys His Val Gln Val Ser Arg Arg Val Leu His Ala Leu Arg Asn Val
385                 390                 395                 400

Glu Gly Tyr Lys Asp Gly Thr Thr Leu Arg Lys Tyr Gly Thr Arg Arg
                405                 410                 415

Pro Thr Gln Lys Asn Lys Val Thr Val Tyr Lys Ser Phe Lys
                420                 425                 430

(2) INFORMATION FOR SEQ ID NO:9:

(i) SEQUENCE CHARACTERISTICS:
        (A) LENGTH: 3 amino acids
        (B) TYPE: amino acid
        (C) STRANDEDNESS: Not Relevant
        (D) TOPOLOGY: linear
```

-continued

```
    (ii) MOLECULE TYPE: peptide (xi) SEQUENCE DESCRIPTION: SEQ ID NO:9:

Gly Asx Asn
```